(12) United States Patent
Laroche

(10) Patent No.: US 9,999,708 B2
(45) Date of Patent: Jun. 19, 2018

(54) PROCESS FOR PREPARING OBJECTS MADE OF BIOCOMPATIBLE HYDROGEL FOR USES THEREOF IN THE MEDICAL FIELD, AND MORE PARTICULARLY IN OPHTHALMOLOGY

(71) Applicant: Laurent Laroche, Paris (FR)

(72) Inventor: Laurent Laroche, Paris (FR)

( * ) Notice: Subject to any disclaimer, the term of this patent is extended or adjusted under 35 U.S.C. 154(b) by 159 days.

(21) Appl. No.: 14/407,506

(22) PCT Filed: Jun. 14, 2013

(86) PCT No.: PCT/IB2013/054874
§ 371 (c)(1),
(2) Date: Dec. 12, 2014

(87) PCT Pub. No.: WO2013/186747
PCT Pub. Date: Dec. 19, 2013

(65) Prior Publication Data
US 2015/0148900 A1  May 28, 2015

(30) Foreign Application Priority Data
Jun. 15, 2012 (FR) ..................... 12 55631

(51) Int. Cl.
| | | |
|---|---|---|
| A61L 27/52 | (2006.01) | |
| A61F 2/14 | (2006.01) | |
| C08F 6/00 | (2006.01) | |
| C08F 6/06 | (2006.01) | |
| C08L 33/20 | (2006.01) | |
| A61F 2/16 | (2006.01) | |
| B29C 67/24 | (2006.01) | |
| C08K 5/20 | (2006.01) | |
| B29K 33/20 | (2006.01) | |
| B29K 105/00 | (2006.01) | |
| B29L 11/00 | (2006.01) | |
| B29L 31/00 | (2006.01) | |

(52) U.S. Cl.
CPC ............. *A61L 27/52* (2013.01); *A61F 2/141* (2013.01); *A61F 2/16* (2013.01); *B29C 67/24* (2013.01); *C08F 6/008* (2013.01); *C08F 6/06* (2013.01); *C08K 5/20* (2013.01); *C08L 33/20* (2013.01); *A61F 2/14* (2013.01); *A61F 2/145* (2013.01); *B29K 2033/20* (2013.01); *B29K 2105/0085* (2013.01); *B29K 2805/00* (2013.01); *B29K 2995/0056* (2013.01); *B29L 2011/00* (2013.01); *B29L 2031/753* (2013.01)

(58) Field of Classification Search
CPC ......... A61F 2/16; A61F 2/145; C08B 37/0039
See application file for complete search history.

(56) References Cited

U.S. PATENT DOCUMENTS 5,273,750 A * 12/1993 Homiger .................. A61F 2/14
424/427
2008/0102276 A1 * 5/2008 Khademhosseini . A61K 9/1652
428/403

FOREIGN PATENT DOCUMENTS

| EP | 0 688 569 A1 | 12/1995 |
| FR | 2 530 638 A1 | 11/1989 |
| FR | 2 810 553 A1 | 12/2001 |

OTHER PUBLICATIONS

Database Compendex [Online] Engineering Information, Inc., New Yourk, NY, US; Dec. 15, 1997, Honiger J et al: "New anionic polyelectrolyte hydrogen for corneal surgery," Database accession No. EIX980-83993684 abstract.
Honiger J et al: "New anionic polyelectrolyte hydrogen for corneal surgery," Journal of Biomedical Materials Research, vol. 37, No. 4, pp. 548-553, Dec. 15, 1997, John Wiley & Sons Inc US.
International Search Report of Application No. PCT/IB2013/054874, issued by European Patent Office dated Nov. 20, 2013.

* cited by examiner

*Primary Examiner* — Stella K Yi
(74) *Attorney, Agent, or Firm* — Arrigo, Lee, Guttman & Mouta-Bellum LLP

(57) ABSTRACT

The present invention relates to a process for manufacturing an object made of biocompatible hydrogel by molding a polymer solution in a mold made of a particular material, said process comprising the following steps:
(i) preparation of a polymer solution by dissolving a copolymer of acrylonitrile and of an olefinically unsaturated co-monomer bearing anionic groups in an aprotic solvent, optionally in the presence of a nonsolvent,
(ii) shaping and the start of gelation of the polymer solution obtained at the end of step (i) in a mold consisting of a material containing said nonsolvent or of a material permeable to said nonsolvent,
(iii) immersion of the object undergoing gelation resulting from step (ii) in a nonsolvent.

The present invention also relates to the objects made of biocompatible hydrogel resulting from this process such as, for example, intracorneal lenses (or lenticules) implantable in the cornea or any other implants usable in ophthalmology.

15 Claims, No Drawings

PROCESS FOR PREPARING OBJECTS MADE OF BIOCOMPATIBLE HYDROGEL FOR USES THEREOF IN THE MEDICAL FIELD, AND MORE PARTICULARLY IN OPHTHALMOLOGY

The present invention relates to a process for manufacturing an object made of biocompatible hydrogel by molding a polymer solution in a mold made of a particular material. The invention also relates to the objects made of biocompatible hydrogel resulting from this process such as, for example, intracorneal lenses (or lenticules) implantable in the cornea or any other implants usable in ophthalmology.

Several processes for making objects in hydrogel for medical and/or surgical use obtained by molding a polymer solution in a mold of suitable shape have already been described in the prior art. Among the latter, we may mention the "spin casting" process, also called centrifugal casting, used by Wichterle (1960) for the manufacture of contact lenses in hydrogel obtained from catalyzed hydroxyethyl methacrylate (HEMA), and whose gelling time depends among other things on the temperature.

Another method for making objects in hydrogels consists of gelation of a polymer solution by cooling to a temperature below the gel point (Patent FR 2 051 147). The main advantage of this process is compensation of the volume change of the polymer solution placed within the mold. This process, which is based on gelation by lowering the temperature below the gel point, does not allow transparent hydrogels to be obtained from an anionic copolymer solution of AN69 (copolymer supplied by the company GAMBRO), but instead leads to translucent hydrogels, which are not usable in refractive ophthalmologic surgery.

Other objects made of hydrogels can be produced by mechanical cutting from a block of hydrogel at room temperature, using blades, micro-saws or lasers, or by cutting with a micro jet of water at very high pressure, or by cryo-machining at very low temperature. This method has also been tested for manufacturing lenses from hydrogel based on AN-69 copolymer, but without success.

The copolymer AN-69 has been used for many years for making hemodialysis membranes (J. Denis et al., Gut, 1978, 19, 787-793). The hydrogel obtained from this copolymer has also been used for encapsulation of the islets of Langerhans in the development of the bio-artificial pancreas (J. Honiger et al., The International Journal of Artificial Organs, 1994, 17, 046-052), or for the encapsulation of hepatocytes with a view to developing a bio-artificial liver (J. Honinger et al., Biomaterials, 1995, 16, 753-759; R. Sarkis et al., Transplantation, 2000, Vol. 70, 58-64; Journal of Hepatology, 2001, 35, 208-216; E. Baldini et al., Transplantation Proceeding, 2009, 41(4), 1367-1369). In studies for treatment of polyarthritis, murine cells have also been encapsulated in a hollow fiber of AN-69 hydrogel (N. Bessis et al., Clin. Exp. Immunol., 1999, 117, 376-382), and in capsules made from this same hydrogel (N. Bessis et al., Rhumatologie, 2003, 70, 855-7). Cells producing erythropoietin have also been encapsulated in hollow fibers of AN-69 hydrogel (E. Payen et al., Haematologica, 1999, 84, EHA-4). Thus, the copolymer AN-69 has already extensively demonstrated its properties of biocompatibility and hemocompatibility, and its capacities for not activating the complement system (J. Honinger et al., J. Biomed. Mater. Res., 1997, 37, 548-553). The hydrogel obtained from this copolymer is also widely used in the field of ophthalmology. Intracorneal lenses have in fact already been made from this copolymer (Patent EP 0 347 267; L. Laroche et al., Macromol. Symp., 1995, 100, 51-55) and implanted in animals, and then evaluated clinically in humans for 20 years already. The same AN-69 hydrogel has also been used for studying the proliferation of epithelial cells for developing lenses for epikeratophakia (F. Maury et al., Journal of Materials Science-Materials in medicine, 1997, 8, 571-576).

The thermoforming of disks of hydrogel for making intracorneal lenses has been employed since the end of the 1980s by J. Honiger and L. Laroche. The optical quality of these lenses was perfect. Before implantation in the cornea, the lenses were decontaminated with peracetic acid, and then rinsed with sterile isotonic solution. The new, more stringent requirements of the Pharmacopeia may specify sterilization, and no longer just decontamination, of implantable objects. When they are sterilized by the prescribed methods, such as damp heat, gamma rays, or accelerated electrons, thermoformed lenses may change shape, and this alters their optical power.

Thus, the weak point of the intracorneal implants obtained from the processes described above is their poor capacity for conserving their shape during the sterilization step.

The applicant has thus endeavoured to supply hydrogels that are transparent and biocompatible, to be used for preparing objects for medical or surgical use that are highly reliable, and in particular for ocular implants with suitable permeability to various biological molecules.

Thus, the first object of the invention is a process for manufacturing an object made of biocompatible hydrogel comprising the following steps:

(i) preparation of a polymer solution by dissolving a copolymer of acrylonitrile and of an olefinically unsaturated co-monomer bearing anionic groups in an aprotic solvent, optionally in the presence of a nonsolvent, (ii) shaping and the start of gelation of the polymer solution obtained at the end of step (i) in a mold having the shape of the desired object, said mold consisting of a material containing said nonsolvent or of a material permeable to said nonsolvent, said step preferably being carried out at room temperature, (iii) immersion of the object undergoing gelation resulting from step (ii) in a nonsolvent, for a sufficient time to allow complete exchange of the solvent with said nonsolvent, and to obtain the object made of hydrogel.

Quite unexpectedly, the applicant found that the use of a mold made of a specific material consisting of nonsolvent and permeable to said nonsolvent made it possible at the same time to ensure exchange between the solvent present in the polymer solution and the nonsolvent at the time of the gelation step, and to form a hydrogel (in the case when the nonsolvent is water) having the desired shape. In fact, it is the presence of the nonsolvent within the mold that causes the molded polymer solution to gel. The ocular and/or intracorneal implants made of hydrogel obtained at the end of the process of the invention display, besides their character of inertness to biological cells:

excellent optical properties: perfect transparency to visible light, absorption of UV radiation, refractive index close to that of the cornea, very good physicochemical properties: high permeability to water, to physiological saline, to small and medium-sized molecules, permeability to dissolved gases, high hydrophilicity, chemical nature without toxic groups, excellent dimensional stability, particular biological properties: non-bioabsorbable in the physiological environment, sterilizable and/or re-sterilizable, good resistance to aging in this environment, good tissue tolerance of the sites of implantation in the corneal stroma (without causing alteration of the corneal epithelium and endothelium), low affinity for proteins.

The dissolution in step (i) may be carried out, with stirring, at a temperature in the range from room temperature to 70° C., and preferably at a temperature of about 50° C.

Step (i) of the process of the invention consists of preparing, by dissolution, an acrylonitrile/co-monomer copolymer advantageously having a molar ratio in the range from 90/10 to 100/0, and preferably in the range from 95/5 to 99/1.

According to an advantageous embodiment, the anionic groups of the olefinically unsaturated co-monomer are selected from the sulfonate, carboxylate, phosphate, phosphonate and sulfate groups.

The acrylonitrile/co-monomer copolymer is advantageously an acrylonitrile-sodium methallylsulfonate copolymer such as the copolymer AN-69 (supplier GAMBRO). These copolymers do not display interaction with the cells and therefore have a greatly improved tolerance.

The aprotic solvent in which the acrylate/co-monomer copolymer is dissolved is advantageously selected from the organic or inorganic polar aprotic solvents, and preferably from dimethylformamide (DMF), dimethylsulfoxide (DMSO), N,N-dimethylacetamide (DMAC), N-methylpyrrolidone (NMP).

The nonsolvent is selected from water, aqueous solutions of mineral salt and aqueous solutions of organic salt.

According to an advantageous configuration of this embodiment, when the nonsolvent is an aqueous solution of salt, said solution is at a concentration between 0.5 and 5 wt %, so as to obtain a concentration of salt between 0.03 and 1 wt %, and preferably between 0.05 and 1 wt %, in the polymer solution.

Even more preferably, the mineral and organic salts are sodium chloride (physiological solution) or potassium chloride, sodium or potassium iodate, sodium or potassium bicarbonate, sodium or potassium chlorate, sodium or potassium periodate, sodium or potassium nitrate, sodium or potassium citrate, sodium or potassium tartrate, sodium or potassium ascorbate, sodium or potassium acetate, sodium or potassium lactate. The preferred aqueous salt solution is a solution of sodium chloride.

According to an advantageous embodiment, the mold in step (ii) is a mold made of hydrogel.

In the sense of the invention, a hydrogel is a material consisting of polymer chains having hydrophilic sites.

The mold in step (ii) may be a mold made of hydrogel based on agarose, alginates, polyhydroxyethyl methacrylate (PHEMA), polyhydroxypropyl methacrylate (PHPMA) or polyacrylate (of sodium or potassium).

Advantageously, the mold in step (ii) consists of:
from 1 to 10 wt %, and preferably from 2 to 6 wt %, of agarose or of alginates, and
from 90 to 99 wt %, and preferably from 94 to 98 wt %, of water or of an aqueous solution of mineral salt or of an aqueous solution of organic salt.

Especially preferably, the mold in step (ii) is a mold made of agarose hydrogel.

In the course of step (ii) of the process of the invention, also known by the term step of "demixing" or step of "phase separation" of the homogeneous polymer solution obtained at the end of step (i), a hydrogel forms.

According to the ternary diagram (copolymer/solvent/nonsolvent), the equilibrium curve separates a zone where the three components are miscible from a zone where the other two phases form (a polymer-rich solid phase, and a polymer-poor liquid phase, or depleted of polymer). In the course of formation of the hydrogel, the system evolves from the initial polymer solution to a composition in which all the solvent is replaced with the nonsolvent, which transforms the gel into a hydrogel. The transition from the liquid form to the gelled form is triggered by contact of the polymer solution with the nonsolvent contained in the mold, with a shape chosen beforehand as a function of the intended subsequent application. The surface layers of the polymer solution that are in direct contact with the surface of the mold containing the nonsolvent begin to gel and take on the shape of the mold. The greater the thickness of the object molded, the longer the gelling time.

Step (iii) of immersion of the object undergoing gelation may be carried out in two steps:
firstly: immersion of the object undergoing gelation in a cold bath of nonsolvent, preferably at a temperature in the range from 0 to 10° C., for a time that may be from 5 to 15 minutes, and
secondly: immersion of the object undergoing gelation in a bath of nonsolvent at room temperature, for a time that may be from 15 to 45 minutes, and preferably for about 30 minutes.

After steps (i) to (iii), the process of the invention may also comprise an optional sterilization step. Advantageously, this sterilization step is carried out by radiation sterilization, for example with gamma rays or with accelerated electrons, and more preferably by radiation sterilization with gamma rays or with accelerated electrons.

The present invention also relates to the objects made of biocompatible hydrogel obtained by the process of the invention.

The term "object made of biocompatible hydrogel" is to be understood as an object manufactured from a nonliving material used as a medical device intended to interact in contact with biological systems, without denaturing them, i.e. without leading to abnormalities in the behavior of cellular tissues and without causing intoxication of the biological fluids circulating in the internal organs of the human or animal body. This contact, which is obvious in the case of an implant, must be extended to the contacts that occur at the surface or on the exterior of the human or animal body, for example those that occur with the blood in the case of hemodialysis or with the cornea in the case of contact lenses.

These objects may be films, threads, rods or implants for medical, biological, ophthalmologic and/or extra-ophthalmologic use.

According to another advantageous embodiment, the objects made of biocompatible hydrogel of the invention are ocular implants. They may be lenses with or without optical or refractive power, and more particularly intracorneal lenses intended to be implanted in the cornea for correcting defects of vision. Especially preferably, the ocular implants of the invention are intracorneal lenses for correcting myopia, hypermetropia, presbyopia, keratoconus or post-LASIK ectasias (iatrogenic keratoconus). Implantation of a lenticule having a defined shape in the cornea, the cornea being for example cut with a femtosecond laser, allows a cornea deformed by keratoconic disease to be remodeled from the inside.

Besides the foregoing arrangements, the invention comprises yet other arrangements that will become clear from the rest of the description given hereunder, which relates to examples demonstrating the improved properties of the objects made of biocompatible hydrogel resulting from the process of the invention.

EXAMPLE

Manufacture of a Contact Lens in Hydrogel of AN-69 Copolymer According to the Process of the Invention Preparation of a Mold Made of Agarose Hydrogel:

The agarose hydrogel mold is prepared from a polypropylene matrix (male part and female part) of a contact lens, supplied by the company Essilor.

An aqueous solution of agarose at 2-4% is prepared by dissolving agarose in isotonic solution (at 0.9% of NaCl in $H_2O$) at a temperature of 80° C. It is then cooled to a temperature of 40-50° C., and poured into the polypropylene matrix (into the two parts separately).

After cooling to room temperature, the two parts of the agarose mold obtained are removed from the mold. The two parts of the mold are then immersed in physiological solution (at 0.9% of NaCl in $H_2O$).

Preparation of a Polymer Solution:

A polymer solution corresponding to the composition shown below is prepared, with stirring, and on a water bath at a temperature of 60° C.:

| Constituents | wt % |
| --- | --- |
| AN-69 copolymer (dry extract) | 9 |
| Dimethylformamide (DMF) | 85 |
| Physiological solution (at 0.9% of NaCl in $H_2O$) | 6 |

Manufacture of a Contact Lens:

A drop of the previously prepared polymer solution is poured into the previously prepared female part of the agarose hydrogel mold. The female part of the mold is closed immediately with the male part.

After 30 seconds, the mold is opened. Extraction of the gelled form of the contact lens is then undertaken. It is immersed twice in succession for 30 minutes in 0.5 L of physiological solution at room temperature, which leads to complete exchange of the DMF (solvent) with the physiological solution (nonsolvent).

A contact lens is thus obtained with a diameter of 10 mm having a thickness at the center of 0.3-0.4 mm. It has an optical power of 2.5 D and an average "water capacity" (water content) of 75%.

The contact lens is then sterilized with gamma rays. The gamma radiation dose absorbed is 25 Gray (or 2.5 MRad).

After sterilization, the contact lens is placed in a capsule containing physiological saline.

The following observations are made:
- the shape of the lens (convex/concave) has not been altered,
- the "water capacity" has decreased by 2%,
- the optical power has changed very slightly (±0.25 D).

The invention claimed is:

1. A process for manufacturing an object made of biocompatible hydrogel, characterized in that it comprises the following steps:
   (i) preparation of a polymer solution by dissolving a copolymer of acrylonitrile and of an olefinically unsaturated co-monomer bearing anionic groups in an aprotic solvent, optionally in the presence of a nonsolvent,
   (ii) shaping and the start of gelation of the polymer solution obtained at the end of step (i) in a mold made of hydrogel,
   (iii) immersion of the object undergoing gelation resulting from step (ii) in a nonsolvent.

2. The process as claimed in claim 1, wherein the acrylonitrile/co-monomer copolymer has a molar ratio in the range from 90/10 to 100/0.

3. The process as claimed in claim 1, wherein the anionic groups of the olefinically unsaturated co-monomer are selected from the sulfonate, carboxylate, phosphate, phosphonate and sulfate groups.

4. The process as claimed in claim 1, wherein the acrylonitrile/co-monomer copolymer is an acrylonitrile-sodium methallylsulfonate copolymer.

5. The process as claimed in claim 1, wherein the aprotic solvent is selected from the organic or inorganic polar aprotic solvents.

6. The process as claimed in claim 5, wherein the aprotic solvent is selected from dimethylformamide (DMF), dimethylsulfoxide (DMSO), N,N-dimethylacetamide (DMAC), N-methylpyrrolidone (NMP).

7. The process as claimed in claim 1, wherein the nonsolvent is selected from water, aqueous solutions of mineral salt and aqueous solutions of organic salt.

8. The process as claimed in claim 7, wherein the nonsolvent is selected from water or an aqueous solution of sodium chloride.

9. The process as claimed in claim 1, wherein the mold in step (ii) is a mold made of hydrogel based on agarose, alginates, polyhydroxyethyl methacrylate (PHEMA), polyhydroxypropyl methacrylate (PHPMA) or polyacrylate.

10. The process as claimed in claim 9, wherein the mold in step (ii) is a mold made of agarose hydrogel.

11. The process as claimed in claim 9, wherein the mold in step (ii) consists of:
    from 1 to 10 wt %, of agarose or of alginates, and
    from 90 to 99 wt %, of water or of an aqueous solution of mineral salt or of an aqueous solution of organic salt.

12. The process as claimed in claim 1, wherein the immersion step (iii) is carried out in two steps:
    firstly: immersion of the object undergoing gelation in a cold bath of nonsolvent, preferably at a temperature in the range from 0 to 10° C., and
    secondly: immersion of the object undergoing gelation in a bath of nonsolvent, at room temperature.

13. The process as claimed in claim 2, wherein the acrylonitrile/co-monomer copolymer has a molar ratio in the range from 95/5 to 99/1.

14. The process as claimed in claim 11, wherein the amount of agarose or of alginates is from 2 to 6 wt %.

15. The process as claimed in claim 11, wherein the amount of water or of an aqueous solution of mineral salt or of an aqueous solution of organic salt is from 94 to 98 wt %.

* * * * *